United States Patent
Iwasaki (12) 
(10) Patent No.: US 6,395,310 B1
(45) Date of Patent: May 28, 2002

(54) **COMPOSITION CONTAINING EMBRYO BUD AND SEED COAT FROM RICE AND FRUIT BODY OF *GANODERMA LUCIDUM* FOR TREATING DIABETES**

(75) Inventor: Teruaki Iwasaki, Sapporo (JP)

(73) Assignee: Kabushiki Kaisha Genmai Koso (JP)

( * ) Notice: Subject to any disclaimer, the term of this patent is extended or adjusted under 35 U.S.C. 154(b) by 0 days.

(21) Appl. No.: 09/982,724

(22) Filed: Oct. 18, 2001

(30) Foreign Application Priority Data

Oct. 24, 2000 (JP) ........................................ 2000-323852

(51) Int. Cl.[7] ............................ A61K 35/78; C12N 1/14
(52) U.S. Cl. ....................... 424/725; 424/750; 424/777; 514/866; 435/254.3
(58) Field of Search ................................ 424/750, 777, 424/725; 514/866; 435/254.3

(56) References Cited

U.S. PATENT DOCUMENTS 5,500,190 A * 3/1996 Andre et al.
5,667,999 A * 9/1997 Koh et al.

FOREIGN PATENT DOCUMENTS

| | | | |
|---|---|---|---|
| JP | 355035052 | * | 3/1980 |
| JP | 59225779 | * | 12/1984 |
| JP | 61135559 | * | 6/1986 |
| JP | 63276450 | * | 11/1988 |
| KR | 9606573 | * | 5/1996 |

* cited by examiner

*Primary Examiner*—David M. Naff
*Assistant Examiner*—Mike Meller
(74) *Attorney, Agent, or Firm*—McKee, Voorhees & Sease, P.L.C.

(57) ABSTRACT

A composition used to treat diabetes is disclosed. The composition is made by first, mixing an isolated embryo bud and isolated seed coat from rice with a fruit body of *Ganoderma lucidum* to form a mixture. Next, the mixture is fermented with an *Aspergillus oryzae* strain to produce a resulting fermentate. Then, the resulting fermentate is dried to produce a dried fermentate. Next, the dried fermentate is crushed into a fine powder and lastly, the powder is mixed with vitamin B to form the composition.

5 Claims, 3 Drawing Sheets

COMPOSITION CONTAINING EMBRYO BUD AND SEED COAT FROM RICE AND FRUIT BODY OF *GANODERMA LUCIDUM* FOR TREATING DIABETES

BACKGROUND OF INVENTION

1. Field of Invention

This invention relates to undevitalized enzyme fortified composition showing suppression against onset of diabetes, and more particularly undevitalized enzyme fortified composition having suppression like a herb-medicine against onset of diabetes in which mixture of embryo bud and seed coat of rice and fruit body of *ganoderma lucidum* are mixed to each other, steamed, aspergillus strain colony is mixed with them, cultivated, ripened, starch and protein are decomposed sufficiently into low molecules and concurrently enzyme groups produced by *aspergills oryzae* strain colony are contained in it as they are, *aspergills oryzae* strain colony contained in the ripened koji is annihilated, they are dried and changed into fine powder under a state in which each of their capabilities of catalysis is not lost, vitamin B groups are added and fortified to them, both suppression action against onset of diabetes and regenerating action of pancreas-$\beta$-cell as well are provided.

2. Description of Related Art

It is estimated that the number of diabetes patients in the world is approximately 60 million and the number of patients accepting administration of insulin as a therapy exceeds 5 million.

In recent years, obesity of children or diabetes of children has become a social problem and additionally obesity or diabetes of pets such as pet dog and the like has also become a social problem.

Increased amount of active oxygen in a human body may cause a certain disorder of cell such as various types of inflammations in lipid, enzyme protein and DNA of biological membranes. For example, $\beta$-cell secreting insulin from a pancreas generates inflammation with .OH, generates a disorder of the cell to cause a secretion of insulin to be weakened, resulting in that a blood sugar value is increased.

Keeping the diabetes as it is without applying any therapy causes a capillary blood vessel in eyes or kidney to show fragility. In the case of type I diabetes of autoimmunization which is called to have onset in a younger generation age, the $\beta$-cell of pancreas secreting insulin may accept attack from $\beta$-limphocyte to decrease in its amount and is gradually diminished. The fact that this diminished $\beta$-cell is not regenerated is an established theory in the medical world.

It is said that since the synthetic insulin for therapy has a different constitutive ratio of amino acid differing from that of a human being, its long term use generates an anti body and its effect shows degradation.

In the case of the type II diabetes, an amount of insulin receptor is decreased due to an increased amount of adipose caused by hyperphagia or obesity (metabolism failure), resulting in that the diabetes becomes the same state as one of a lack of insulin. As the blood sugar value is increased, the $\beta$-cell of pancreas may generate insulin, although it may become a chronic inflammation due to functional impoverishment.

As derangement of metabolism function concerning nourishment, reduction in carbohydrate metabolism function is a typical one and it has a substantial meaning as an index for setting an ageing.

As a high ageing tendency has been promoted in the society, an age in which a degradation of carbohydrate metabolism function of a human shows a peak value is about 65-years old, the derangement of nutritional metabolism may cause a lack of energy, it becomes a major cause of disorder in a health condition, resulting in producing a series of syndromes and further it may also become a major cause of the type II diabetes of which much cases are found in high-aged persons. These topics have become a future substantial theme in a high-aged society.

Medicines for healing diabetes have been studied and the gazette of Japanese Patent Publication No. Hei 8-40 has a description that the medicines are utilized for healing diabetes. However, no practical description about it is not found in this gazette. The composition that can be easily taken, has no side effect and has a certain pharmacodynamic effect in regard to the suppression against onset of diabetes has not yet confirmed.

The present inventor has studied several times about nutrients of embryo bud of rice and fruit body of *ganoderam lucidum* and in particular sugar chain of protein contained in these foods in view of the fact that sugar chain substantially concerns with inter-cell acknowledgement in the metabolism or cell constituting insulin, glucagon, with the result that the present inventor has confirmed that the composition containing enzyme groups keeping capability of catalysis of enzyme proper attained by mixing embryo bud of rice and fruit body of *ganoderma lucidum* to each other to cultivate *aspergills oryzae* strain colony and ripen them has some superior pharmacodynamic effects of suppression against onset of autoimmunization type I diabetes. In addition, the present inventor has completed the present invention in reference to knowledge that synergism caused by concurrent intake of vitamin B groups, in particular, vitamins $B_1$, $B_6$, $B_{12}$, vitamin C and vitamin E acting coenzyme may improve effect more.

SUMMARY OF INVENTION

In order to solve the aforesaid problems, the present invention has employed such a technical means.

That is, mixture of embryo bud and seed coat, *ganoderma lucidum* having its fruit body crushed therein and rice particles as desired are mixed to each other, steamed, *asperills oryzae* strain colony is dispersed onto them, cultivated and ripened, thereafter species in ripened koji, and further they are changed into dried fine powder while enzyme groups may not lose capability of catalysis of enzyme proper, vitamin B groups are added to the dried fine powder to make composition, and when a person takes a specified amount of this composition, environment of bio-tissue cell is improved more superior as synergism effect, energy is given to the tissue cell to activate metabolism function and immunity function as well and the suppression against onset of diabetes can be effectively attained.

Although a physiological meaning of sugar chain of glycoprotein at internal cell is not explicated well yet, it can be considered that function of sugar chain already known is deeply concerned with cognizance of inter-cell caused by difference in shape of sugar chain in tissue cell, migration in the internal organism along with the cognizance and protein metabolism of cell, inflammation caused by active oxygen or bacterium or the like may induce change in sugar chain, cognance disability of inter-cell and disturbance in receptor and these phenomena cause immunodeficient or decompensation or the like. It is acknowledged that a cause of immunodeficient consists in a reduction in metabolism function of erythrocyte or leukocyte and a lack of energy, and it is called that an improvement of environment of the internal cell by supplementing sufficient nutritive substance becomes a substantial power for improving sickness.

The composition of the present invention is based on the facts described above.

The "undevitalized enzyme" expressed in the text of the present invention is defined as enzyme in which capability of catalysis of various kinds of enzyme generated by *aspergills oryzae* strain colony is not lost.

The "ripening" described in the text of the present invention is defined as a processing in which macromolecules such as starch, protein or the like in particular are sufficiently decomposed into low molecules by various kinds of enzymes secreted by *aspergills oryzae* strain colony. The "product temperature" is defined as a temperature of raw material where species bacteria (*aspergills oryzae*) is cultivated at a culture bed to generate heat. The "raw material" is defined as material generating this composition of suppression. In addition, the "requisite raw material" is defined as vitamins, excipient material, and special additive raw material added to the dried powder before the powder is solidified. The "special raw material" is defined as a tasting material, an odor material and fortified nutritive substances.

Practical configuration of the present invention is as follows.

(1) Undevitalized enzyme fortified composition in which starch and protein contained in mixed raw material of mixture of embryo bud and seed coat of rice and fruit body of *ganoderma lucidum* are decomposed into low molecules by *aspergills oryzae* strain colony, and are changed into dried fine powder with a moisture content of 4% or less under a state in which enzyme groups generated by *aspergills oryzae* strain colony are contained as they are and the enzyme groups do not loose capability of catalysis, vitamin B groups are added to and mixed with the dried fine powder and each of the enzyme groups holds the capability of catalysis of the enzyme proper.

(2) Undevitalized enzyme fortified composition in which starch and protein contained in mixed raw material of mixture of embryo bud and seed coat of rice and fruit body of *ganoderma lucidum* are decomposed into low molecules by *aspergills oryzae* strain colony, and are changed into dried fine powder under a state in which enzyme groups generated by *aspergills oryzae* strain colony are contained as they are and the enzyme groups do not loose capability of catalysis, one or more selected from vitamin $B_1$: 2 mg to 100 mg
vitamin $B_6$: 5 mg to 100 mg
vitamin $B_{12}$: 3 μg to 1500 μg is added to and mixed per 20 g of the dried fine powder, and each of the enzyme groups holds capability of catalysis of the enzyme proper.

(3) Undevitalized enzyme fortified composition in which starch and protein contained in mixed raw material of mixture of embryo bud and seed coat of rice and fruit body of *ganoderma lucidum* are decomposed into low molecules by *aspergills oryzae* strain colony, and are changed into dried fine powder under a state in which enzyme groups generated by *aspergills oryzae* strain colony are contained as they are and the enzyme groups do not loose capability of catalysis, vitamin $B_1$: 2 mg to 100 mg
vitamin $B_6$: 5 mg to 100 mg
vitamin $B_{12}$: 3 μg to 1500 μg are added to and mixed per 20 g of the dried fine powder, and each of the enzyme groups holds capability of catalysis of the enzyme proper.

(4) Undevitalized enzyme fortified composition according to any one of claims (1) to (3) in which vitamin C of 50 mg to 600 mg per 20 g of the composition is added.

(5) Undevitalized enzyme fortified composition according to any one of claims (1) to (4) in which vitamin E of 10 mg to 300 mg per 20 g of the composition is added.

(6) Undevitalized enzyme fortified composition in which starch and protein contained in mixed raw material of mixture of embryo bud and seed coat of rice, fruit body of *ganoderma lucidum* and unpolished rice are decomposed into low molecules by *aspergills oryzae* strain colony, and are changed into dried fine powder under a state in which enzyme groups generated by *aspergills oryzae* strain colony are contained as they are and the enzyme groups do not loose capability of catalysis, special raw materials such as tasting agent and odor agent are added to the dried fine powder and the composition is formed into solid material by excipient material.

BRIEF DESCRIPTION OF DRAWINGS

Preferred embodiments of the present invention will be described in detail based on the followings wherein.

DETAILED DESCRIPTION

1. Description of Preferred Embodiments

The preferred embodiments of the present invention will be described as follows.

Embryo bud and seed coat portions of rice occupy about 5% of entire unpolished rice. As the type of rice applied in the present invention, unpolished rice (black rice, red rice) and glutinous rice can be applied in addition to normal rice. The embryo bud and seed coat portions of rice contain phytin acid, arabinoxylan, ferulic acid, inositol, GABA (4-aminobutyric acid), polysaccharide, antioxidant and unsaturated fatty acid or the like in addition to glycoprotein, minerals or vitamins.

Arachidonic acid in unsaturated fatty acid is a precursor for biosynthesis of physiological activator, i.e. prostaglandin (hereinafter referred to "PG"), in a human body. The PG has ten types A to J, and this substance is called as topical hormone having actions such as prohibition of coagulation of plasma, vasohypotonia and suppression against arteriosclerosis and the like.

In the case of hyperlipidemia or hypertension that is one of complications of diabetes, it is called that if synthesis of $PGI_2$ is not in time for it, blood platelet is coagulated to generate thrombus.

Preferred embodiment 1 of a manufacturing method of the present invention will be described as follows.

Mixture of embryo bud and seed coat of selected rice is put into a water-supplying machine, sufficient amount of water is absorbed into the mixture to cause it to be bulged. The bulged mixture is put into a steamer, fruit body of *ganoderma lucidum* (which is also called as "Reishi" in a harb medicine) crushed with its grain size being about 3 mm is added by about 5 wt % to 20 wt % of its entire volume, calcareous powder (baked oyster shell with a grain size No. of 250 mesh to 400 mesh) is added by about 0.5 wt % to 1.2 wt % of entire volume and they are steamed by steam of 100° C. to 120° C. for about 50 to 60 minutes while its moisture is being checked.

It is well known in a medical world that much amount of polysaccharide (macromolecule sugar chain) contained in fruit body of *ganoderma lucidum* may activate leukocyte, cause hormone-related tissues to be active and further activate immunity function.

Fruit body of *ganoderma lucidum* includes many types of polysaccharides (arabinoxyloglucan, xylogalactoglucan, β-D-glucan, acid-β-glucan, acid hetero-β-glucan, acid xylo-β-glucan, protein-bound xylomanno-β-glucan, manno-β-glucan, arborescent β-D-glucan, heteroglucan, peptideglucan, fucofructose glucan and others).

The raw materials described above are steamed together with calcareous powder to cause a potency of protease of the raw material under cultivation of species bacteria to be increased by several times.

The steamed raw materials are transferred automatically to a cooling device, released to be cooled down to about 37° C. to 40° C., further transferred automatically to a mixing device, the species bacteria strain colony of about 1/1000 of raw material by weight is added and they are well mixed to each other.

As species bacteria, *aspergills oryzae* strain colony is mainly applied and species bacteria strain colony selected from other koji bacteria strains (for example, *A. kawachii, A. awamori, A. usamii*) having different characters can be mixed within a range of 25% to 30%.

Each of the aforesaid species bacteria strain colony secretes decomposing enzymes to decompose starch and protein or the like into low molecules. A temperature suitable for cultivation of species bacteria strain colony is about 35° C. to 37° C., its humidity is about 85%RH to 90%RH and activation of species bacteria under a humidity value of 70%RH or less is stopped. When the temperature exceeds 42° C., almost of the species bacteria become extinct.

The raw materials mixed with species bacteria strain colony are transferred automatically to a closed type box-like temperature/humidity adjusting machine, both temperature and humidity are adjusted in a stepwise manner within atmosphere at a culture bed of about 35° C. to 37° C. and a humidity of about 95%RH to 99%RH and further it is cultivated from about 32 hours to 36 hours.

The temperature and humidity-adjusting machine is provided with an automatic measuring and recording device for a product temperature (a temperature of raw material during cultivation of rice koji aspergillus) in addition to an automatic air conditioner and a humidity-adjusting device. It is also provided with an automatic agitating device and an automatic smoothing device and the like.

At the temperature/humidity adjusting machine, a product temperature of the culture bed in a lag phase promoting species bacteria strain colony is gradually increased automatically from 25° C. to 38° C. through aspergills cultivation heat. This state is kept for a minimum duration period of 8 hours. When a product temperature of the culture bed (a temperature of raw material in the aspergillus culture bed) is about 40° C. to 41° C., the culture bed is agitated and forcedly contacted with fresh air to decrease a product temperature in such a way that the activation of species bacteria may not be made dull under over-heating condition. At this time, the product temperature decreases down to about 32° C. and it is increased again up to a certain temperature with generated heat under cultivation of species bacteria strain colony.

A growing phase promoting ripening of the species bacteria strain colony is monitored under an atmospheric temperature of about 31° C. to 36° C. so as not to cause the product temperature to exceed 40° C., and when the product temperature becomes about 40° C. to 42° C. after six hours, the culture bed is agitated to decrease the product temperature and the culture bed is agitated to cause the product temperature to become in a range of about 39° C. to 40° C., thereby both temperature and humidity are adjusted and cultivation is carried out for about 11 to 12 hours.

Species bacteria secretes amylase of starch decomposing enzymes, protease of protein decomposing enzymes, and lipase of fat decomposing enzymes, and decomposes the raw materials into low molecules to attain nutritious substances from them. Fruit body of *ganoderma lucidum* having cell membrane softened is processed such that its solid cell wall is decomposed by cultivation of the species bacteria strain colony and polysaccharide may easily be absorbed.

Since the species bacteria is aerobe in its characteristic, the culture bed is agitated by three to four times for every specified hours (8 hours) to supply oxygen to it and its color and odor are checked. In addition, the ripening and a degree of dried state are adjusted by adjustment of both temperature and humidity in a temperature/humidity-adjusting machine and by agitation of the culture bed.

As to the raw materials such as embryo bud, seed coat and *ganoderma lucidum* or the like described above, although it is satisfactory that the species bacteria may be individually cultivated, if they are cultivated under a state in which each of the raw materials is mixed to each other, enzyme groups generated by the species bacteria are activated to each other, resulting in that synergistic effective decomposition and coupling are produced.

During a rest phase in which growing of species bacteria is prohibited, it is adjusted to have a humidity of 70%RH or less where activation of species bacteria strain colony becomes dull, and further a temperature of the atmosphere is also increased up to about 36° C. to 37° C. It is adjusted within a range of about 39.5° C. to 40° C. and it is ripened for about 6 hours. At this time, a value of pH of the culture bed is kept at a value less than 6 to 7. During this period, the raw materials are completely decomposed into low molecules by the enzyme groups secreted by the species bacteria strain colony and ripened.

After this processing, the raw materials in which the embryo bud, seed coat and *ganoderma lucidum* or the like are cultivated, ripened and changed into low molecules in the culture bed are dried in atmosphere of about 46° C. to 50° C. for about 8.5 to 9.5 hours. The product temperature is controlled in a range of about 44° C. to 46° C., activity of species bacteria strain colony is completely stopped and the species bacteria strain colony becomes extinct. Under the condition of atmosphere and product temperature as described above, capability of catalysis of the enzyme groups is not lost. With such an arrangement as above, ripening with the enzyme groups is sufficiently carried out.

Upon completion of drying processing, the ripened koji becomes a dried and ripened koji with its contained moisture being 4% or less and about 2.5% to 3.6%. In this connection, contained moisture of distributed rice is about 14% to 15%.

The dried and ripened koji is filtered through a screen to remove block-like solid material with a size of 5 mm or more, presence of foreign material in it is checked, the koji is applied to a crushing machine and is changed into fine powder while a degree of fine powder is being checked and then the material is applied to the screen and the presence of the foreign material is checked. Changing the material into the fine powder causes the substances such as embryo bud and ganoderma lucidum in the composition to be mixed with their distribution being uniform.

The preferred embodiment 1 of the undevitalized fortified composition with a raw material mixing rate acting as a basic product is as follows.

| | |
|---|---|
| Embryo bud of rice | 85 wt % |
| Ganoderma lucidum | 14 wt % |
| Calcareous powder | 1 wt % |

And as an allowable range, they can be mixed as follows.

When the mixture of embryo bud and seed coat is of about 80 to 92 wt %,

| | |
|---|---|
| Ganoderma lucidum | 8 wt % to 20 wt % |
| Calcareous powder | 0.5 wt % to 10 wt % | provided that when an amount of calcareous powder is increased, the calcareous material with a large grain size is put into a bag and steamed, and after steaming operation, the calcareous material is removed.

An acid value of the dried fine powder of basic product manufactured in this way was about 48.2 to 51.3. In addition, analyzed total titer of enzyme per 100 g of basic product composition concerning lipase of fat decomposing enzyme, amylase of starch decomposing enzyme and protease of protein decomposing enzyme was as follows.

| | |
|---|---|
| Titer of lipase | 565 U/g to 572 U/g |
| Titer of amylase | 2300 U/g to 2900 U/g |
| Titer of acid protease | 186 U/g to 237 U/g |
| Titer of neutral protease | 343 U/g to 408 U/g |
| Titer of alkaline protease | 187 U/g to 218 U/g |

Further, an amount of inclusion of vitamins and minerals under analyzed total amount per 100 g of fine powder was as follows.

| | |
|---|---|
| Vitamin A effective | 3786 IU to 4639 IU |
| Vitamin $B_1$ | 1.7 mg to 1.8 mg |
| Vitamin $B_2$ | 0.64 mg to 0.67 mg |
| Vitamin $B_6$ | 2.33 mg to 2.41 mg |
| Vitamin $B_{12}$ | 0.5 $\mu$g to 0.6 $\mu$g |
| Vitamin E | 14.1 mg to 14.9 mg |
| Pantothenic acid | 7.08 mg to 7.10 mg |
| Folic acid | 0.17 mg to 0.18 mg |

-continued

| | |
|---|---|
| Biotin | 44.8 $\mu$m to 47.5 $\mu$m |
| Iron | 7.5 mg to 7.7 mg |
| Zinc | 4.43 mg to 5.66 mg |

As applied rice, three kinds of rice from different producing districts were mixed. As ganoderma lucidum, a plurality of kinds of ganoderma lucidum from different producing districts were mixed. As calcareous powder, baked oyster shell powder was selected, although its raw materials such as bone powder, lactic acid calcium, crab shell are not limited at all.

As for the dried fine powder, a desired reference amount of each of vitamins is added.

Although vitamin $B_1$ is antineutritis factor and antiberiberi factor, this vitamin $B_1$ may also act biochemically as coenzyme of decomposing enzyme against pyruvic acid, 2-ketoglutelin acid and the like. A healthy amount per day for an adult person is about 2 mg and a large amount of it is used for a therapy, for example, 100 mg/day is used. Vitamin $B_6$ is deeply concerned with amino acid metabolism and acts as antiallergy factor. It may act in the organism as coenzyme such as amino acid decarboxylase enzyme, amino acid racemase or the like. A desired amount per day for an adult person is about 3 mg, and as its dose about 5 to 100 mg per day is used.

It is said that vitamin $B_{12}$ is antipernicious anemia factor that is essential for biosynthesis of protein and deeply concerned with biosynthesis of nucleic acid. A desired amount per day for an adult person is about 2 $\mu$g and a dose for therapy is about 1000 $\mu$g to 1500 $\mu$g.

Vitamin C is concerned with both oxidation and reducing actions in living thing, and assists in action in hydrogen transmission enzyme system. A desired amount per day is 70 to 75 mg and a desired amount for therapy is about 300 mg to 600 mg.

Vitamin E is antioxidant and improves peripheral vascular lesion. A desired amount per day is about 3 mg to 10 mg and a desired amount for therapy is 100 to 300 mg.

As a preferred embodiment for mixing of vitamins, there are provided one case in which three types of

| | |
|---|---|
| Vitamin $B_1$ | 2 mg to 100 mg |
| Vitamin $B_6$ | 5 mg to 100 mg |
| Vitamin $B_{12}$ | 3 $\mu$g to 1500 $\mu$g | are combined to each other and the other case in which

| | |
|---|---|
| Vitamin C | 50 mg to 600 mg |
| Vitamin E | 10 mg to 300 mg | are combined to each other per 20 g of the composition (for one-day dose) in addition to these three types of former vitamins.

In addition, although there are some cases in which any one of groups of vitamin B (preferably vitamin $B_{12}$ is not excluded), vitamin C and vitamin E are combined to each other, a combination of five kinds of vitamins is preferable. It is natural to say that folic acid, biotin, nicotinic acid and pantothenic acid and the like can be selected from other groups of vitamin B and combined to each other.

The dried fine powder mixed with vitamins is automatically measured, fed into a can, the can is sealed and this dried fine powder is sold as a powder agent.

In addition, excipient material to be described later is added to the aforesaid dried fine powder, the fine powder is formed into particles with a grain size of about 1.2 mm to 1.3 mm by a granulating machine, and after drying operation, it is packaged in a bag with one package weight being 3.5 g or 4 g and the like, for example, by a folding machine to make a granule agent. Or the powder is not formed into granules, but formed into a tablet with one tablet being 1 g by a tablet-forming machine.

As a preferred embodiment 2 of mixed raw materials, a mixing amount of raw materials is as follows.

| Mixture of embryo bud and seed coat of rice | 80 wt % |
|---|---|
| Ganoderma lucidum | 10 wt % |
| Unpolished rice | 10 wt % |

These materials are mixed to each other, and concurrently steamed to cultivate the species bacteria strain colony. In the case of this product, a titer of neutral protease was increased by about 38 U/g to 43 U/g.

As special products providing synergistic in view of herb medicine, special additives can be added to and mixed with the aforesaid powder composition under the following mixing rate or optional combination to have a total weight of 100%.

| Spirulina | 3 wt % to 8 wt % |
|---|---|
| Glucan liquid | 3 wt % to 6 wt % |
| Sea weed power (as a source of yode) | 1 wt % to 3 wt % |

The aforesaid spirulina is a kind of bluealgae proliferated well in salt water, has chlorophyll, and 60% of its entire volume is protein having stable amino acid. The aforesaid glucan liquid is polysaccharide extraction liquid extracted from unicellular bluealgae and its solid component is 0.5% to 1.0%. As for domestic dogs, animal protein such as dried meat, dried fish and dried bonito powder can be added to the product by about 2 to 5 wt % in order to apply odor and taste. In the case of use for the domestic dogs, the product is sprinkled over feed or mixed with the feed at a rate of about 0.18 to 0.35 g per 1 kg of dog weight in a day. The aforesaid powder or granules can be mixed with appropriate excipient material and further can be formed into a biscuit-like solid material that the dogs can easily eat.

With such a configuration as described above, the following raw materials are selected as excipient material within a range of mixing rate, they are mixed before forming granules (forming tablet) and they are formed into granules or tablets.

| Glucose | 4 wt % to 12 wt % |
|---|---|
| Lactose | 12 wt % to 20 wt % |
| Vegetable oil and fat | 2 wt % to 6 wt % |

As for the function to suppress onset of diabetes provided by undevitalized enzyme fortified composition of the present invention, the present inventor performed the following experiment about the suppression against onset of diabetes under application of "NOD mouse", which is a model animal for autoimmunization type I diabetes.

(1) Tested Experiment Animal

NOD/Crj, female (a male mouse in this family scarcely shows onset)

(2) Applied Composition

Undevitalized fortified composition including *garnoderma lucidum* by 10 wt % was resolved in diluted water for sterilization injection and used.

(3) Groups of Experiment (a) Tested Groups

Diluted water for sterilization injection was fed through a mouth by 10 mg/g weight with a gastro probing needle in the evening from Monday to Friday.

(b) Applied Groups

Constitution was dissolved in diluted water for sterilization injection by 0.33 mg/g weight per day and fed through a mouth with a gastro probing needle in the evening from Monday to Friday.

As for both groups (a) and (b), radiation irradiated solid feed is continuously supplied.

(4) Feeding Density

| 5 mice or less/cage | (a) Tested groups: 15 mice, 3 cages |
|---|---|
| | (b) Applied groups: 15 mice, 4 cages |

(5) Experimental Period

Continuous 20 weeks from four-week age.

(6) Test Items in Experimental Period

Weight measurement: Once/one week-Individual mouse was discriminated with an ear piercing method. Measured at every Thursday.

Blood sugar measurement: Once/four weeks-blood sugar measurement method-easy blood sugar measuring unit (a glucose sensor)

Urine sugar test and confirmation of onset: Urine sugar test was performed from 13-week age at a frequency of 2 to 3 times/week Further, as to the individual experiment animal, (a) Blood sugar value was directly measured.

(b) Onset was acknowledged in the case of a relation of blood sugar value >200 mg/dl.

(c) As to the onset individual mouse, some organs such as pancreas, hepato and livers were totally extirpated after full blood was taken (heparin processing)(a histological retrieval).

(d) A urine sugar test paper was used for a urine sugar test.

(e) Anatomy was carried out in reference to a case taking separately made.

Results of the aforesaid experiment were as follows.

(a) Cumulative onset rate of the tested groups was 53.3% at the time of completion of experiment (at the age of 175-day).

(b) Cumulative onset rate of the applied groups was 11.1% even at the time of completion of experiment (at the age of 175-day) and an onset suppression effect in statistical point of view was acknowledged.

(c) Cumulative onset rate of I type diabetes of the applied groups was acknowledged in onset suppression effect from the age of 167-day as compared with that of the tested groups (refer to Table 1).

TABLE 1

As apparent from this Table 1, the onset of the type I autoimmunization diabetes was acknowledged in the tested groups from 132-day age, the onset rate was rapidly increased from the 156-day age and, the onset rate of about five times of the type I autoimmunization diabetes was indicated at the 175-day age as for the applied groups.

In the applied groups, onset of type I autoimmunization diabetes is acknowledged after 145-day age, an onset rate from 152-day age to 175-day age shows a stable value of about 11.1% and it is acknowledged that the onset suppression effect of type I autoimmunization diabetes appears in a stable and positive manner.

That is, as compared with the applied groups, it is clearly acknowledged that the applied groups have a pharmacodynamic effect for suppressing the cumulative onset rate of type I autoimmunization diabetes to about ⅕.

Such a remarkable result is not acknowledged in any kinds of prior art medicines.

The present inventor has studied immunohistochemistry alteration of Langerhans island in pancreas of NOD mouse fed with the undevitalized enzyme fortified composition of the present invention. Insulin generating cell is dyed with insulin antibody into a charcoal color, other cells than the insulin generating cell are dyed into red under application of mixed three kinds of antibodies (antiglucagon, antisomatostatin and anti-pancreatic polypeptide) and a result of observation with an electron microscope is as follows.

Applied groups: A high Langerhans island inflammation was observed in all individuals. In the Langerhans island of the infammated individual, a tissue image where only the generating cells other than insulin generating cell are collectively present was observed. In the non-infammated individual, Langerhans island of only the generating cell other than insulin generating cells (FIG. 1: a photograph A) and Langerhans island where a slight amount of insulin generating cell is present (FIG. 2: a photograph B) were observed under an approximate similar ratio.

The groups applied with composition of the present invention: Outgrowth of epithelial cell of conduit of pancreas was remarkable. Further, in the case of epithelial cell of the conduit of pancreas, insulin generating cells and generating cells other than insulin (refer to FIG. 3: a photograph C and FIG. 4: a photograph D) were dispersed. In addition, a group of insulin generating cells that they are divided and proliferated from the epithelial cell of conduit of pancreas (refer to FIG. 3: a photograph C indicated by an arrow) was frequently observed. Such an increased tissue was not acknowledged in the applied groups.

Figure 1:
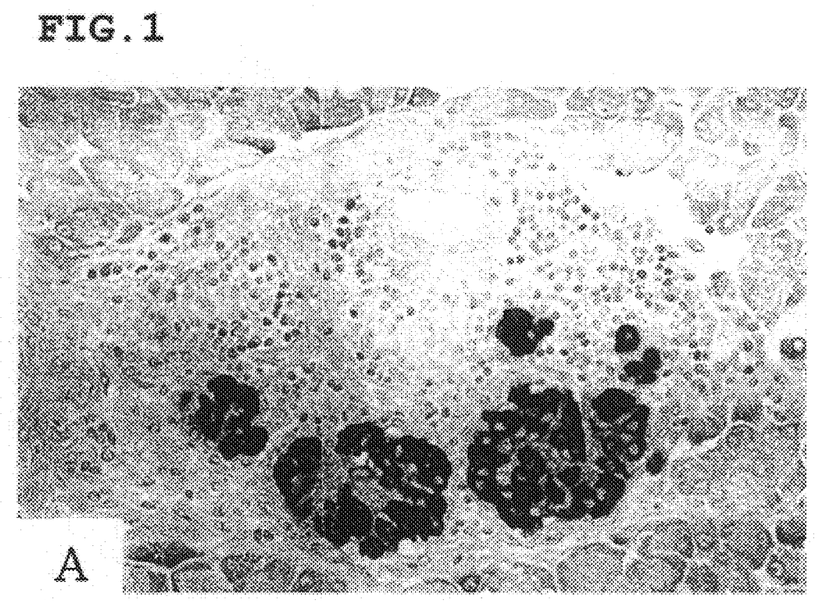
FIG. 1 is an electron microscopic photograph for showing Langerhans island of only a generating cell other than insulin generating cell.
Figure 2:
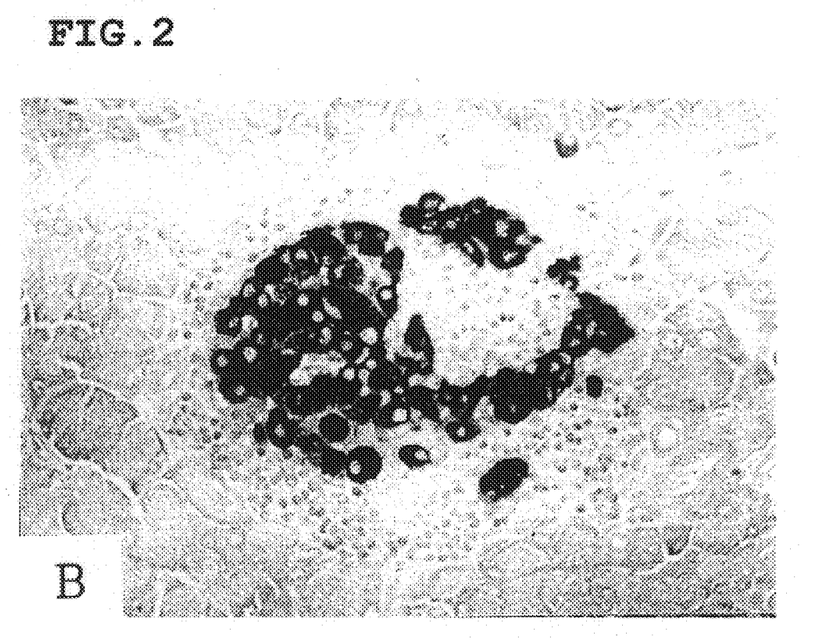
FIG. 2 is an electron microscopic photograph of Langerhans island where insulin generating cell is present.
Figure 3:
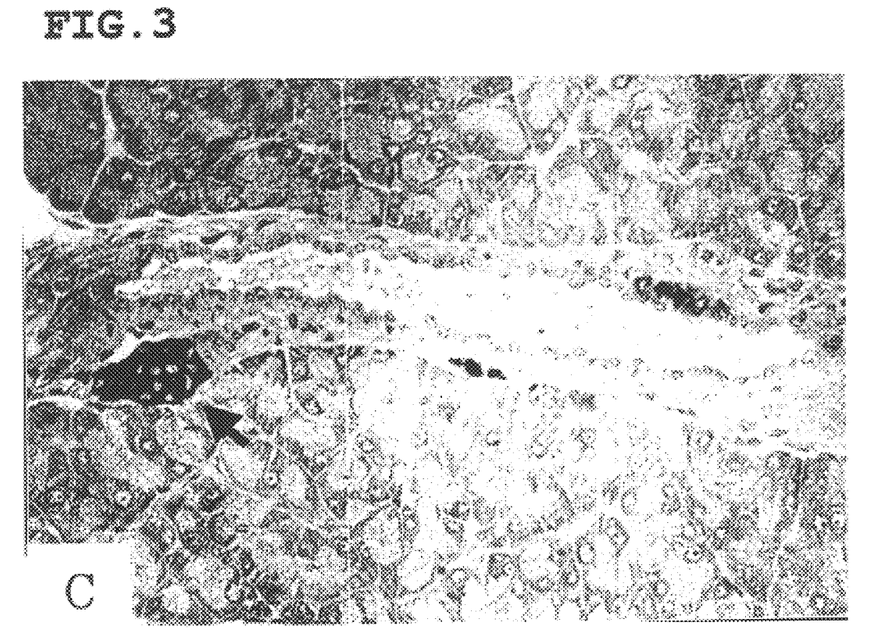
FIG. 3 is an electron microscopic photograph for showing an insulin generating cell and another generating cell except insulin, wherein an arrow indicates a group of insulin generating cells where an amount of tissues is increased.
Figure 4:
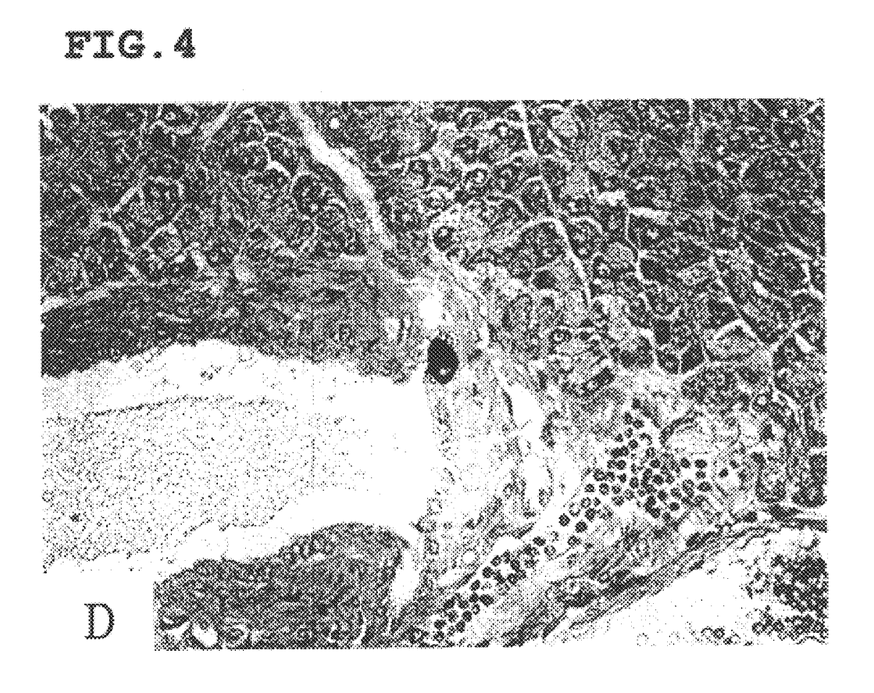
FIG. 4 is an electron microscopic photograph for showing an insulin generating cell and another generating cell except insulin.
Figure 5:
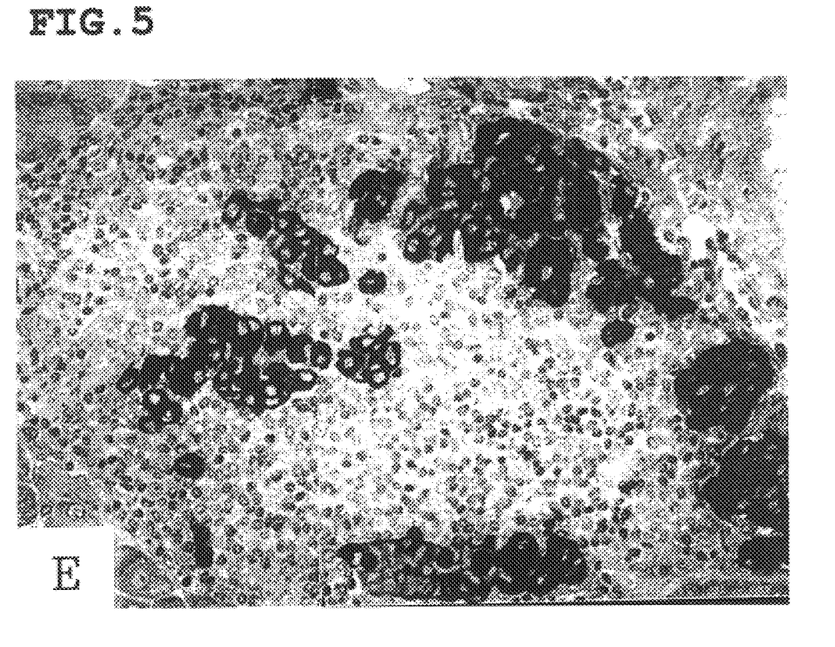
FIG. 5 is an electron microscopic photograph showing a state in which inflammation of Langerhans island is observed and residual insulin generating cells are present.
Figure 6:
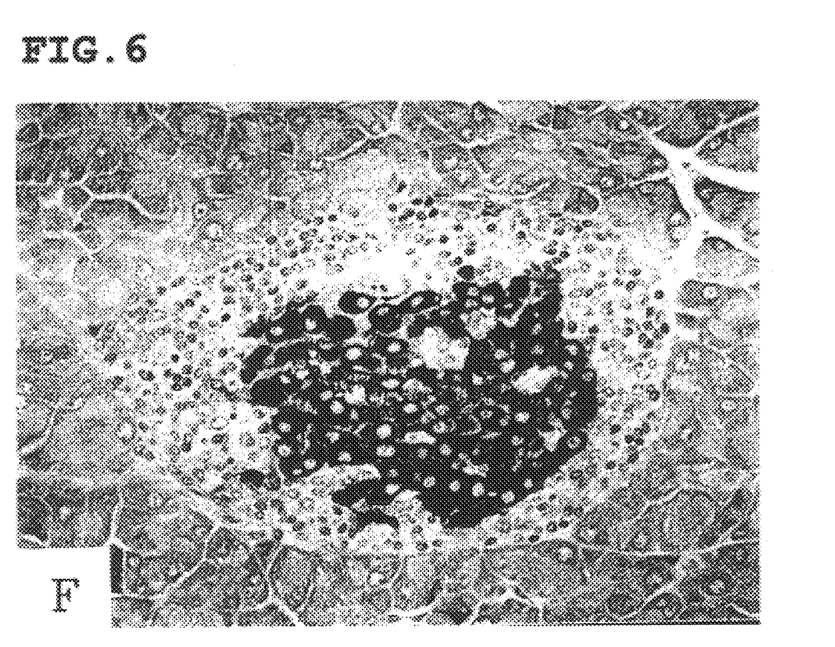
FIG. 6 is an electron microscopic photograph showing a state in which inflammation of Langerhans island is observed and residual insulin generating cells are present.

Further, although the high inflammation of Langerhans island was observed in the same manner as that of the applied groups, the residual insulin generating cells were apparently much more than that of the applied groups (FIG. 5: a photograph E and FIG. 6: a photograph F).

This fact indicates that applying the undevitalized enzyme fortified composition of the present invention may suppress inflammation of β-cell of pancreas secreting insulin and effectively provide regenerative recovery, and it is apparently recognized that the composition may have a superior pharmacodynamic in view of herb medicine acting as a composition for suppressing the onset of diabetes.

Then, although it was called in the prior art that these diminished cells are not regenerated, it was proved that improved environment of cells through a well-balanced intake of nutrient substances causes these cells to be regenerated, differentiated and proliferated.

This can be estimated that complex actions and nutrient substances such as much amount of vitamins, minerals, plenty of groups of enzyme and special substances contained in the undevitalized enzyme fortified composition of the present invention contributed to improvement of environment of the cells of body tissues, gave energy and activated metabolism.

An amount of applying the composition to the aforesaid mouse corresponds to about 21 g per day as compared with that of a human having a weight of 60 kg.

As complication of the type II diabetes, this complication is highly concerned with hypertension, diabetes, arteriosclerosis, cerebral infarction, angina pectoris and hyperlipidemia in myocardial infarction (high cholesterol, high neutral fat). As for the effect of suppression of undevitalized fortified composition of the present invention in regard to this hyperlipidemia, examples of clinical data attained by an adviser doctor of the present applicant will be indicated as follows.

As a trial composition, the applicant compared between "a composition I" in which the composition is not fortified with vitamins and "a composition II" in which the composition is fortified with vitamins.

In the case of the composition II, vitamin $B_1$ of 100 mg, vitamin $B_6$ of 100 mg, vitamin $B_{12}$ of 1000 μg, vitamin C of 400 mg and vitamin E of 200 mg were mixed with this composition of 20 g, respectively.

CLINICAL EXAMPLE 1

Adult male (age: 66) with diabetes for ten-odd years; neuritis of diabetic membrum inferius; and postprandial blood sugar value of 337 mg/dl (200 mg/dl or less is preferable).

Upon continuous feeding of the composition I of the present invention by 20 g every day, the blood sugar value became 302 mg/dl on the 10th day. Also his dolor of membrum inferior was mitigated.

Upon continuous feeding of the composition II of the present invention by 20 g every day, the blood sugar value was changed from 302 mg/dl to 256 mg/dl on the 10th day. Also his blood pressure was stabilized in a range of 143 mmHg to 96 mmHg.

CLINICAL EXAMPLE 2

Adult male (age: 65) with diabetes and complication of hepatosis:

He continued to take the composition I of the present invention by 20 g every day. The blood sugar value was decreased from 341 mg/dl to 305 mg/dl on 10th day. Neutral fat was also decreased from 280 mg/dl to 235 mg/dl.

He continued to take the composition II of the present invention by 20 g every day. The blood sugar value was decreased from 305 mg/dl to 248 mg/dl on 10th day. Neutral fat was also decreased from 235 mg/dl to 176 mg/dl.

CLINICAL EXAMPLE 3

Adult female (age: 61) with hyperlipidemia and chronic hepatitis:

She continued to take the composition I of the present invention by 20 g every day. Cholesterol was decreased from 251 mg/dl to 228 mg/dl on 35th day. Neutral fat was also decreased from 372 mg/dl to 249 mg/dl.

She continued to take the composition II of the present invention by 20 g every day. Cholesterol was decreased from 228 mg/dl to 201 mg/dl on 10th day. Neutral fat was also decreased from 249 mg/dl to 219 mg/dl.

CLINICAL EXAMPLE 4

Adult female (age: 63) with diabetes, blood sugar value at her hungry state of 308 mg/dl (normal value is 110 mg/dl or less):

Upon continuous feeding of the composition I of the present invention by 20 g per day without taking any internal medicine, her blood sugar value was changed to 243 mg/dl on 21th day.

Upon continuous feeding of the composition II of the present invention by 20 g per day, her blood sugar value was also changed from 243 mg/dl to 178 mg/dl on 14th day.

CLINICAL EXAMPLE 5

Adult female (age: 57) with diabetes, hyperlipidemia, blood sugar value at her hungry state of 153 mg/dl and neutral fat of 465 mg/dl.

She continued to take the composition I of the present invention by 20 g every day. Her blood sugar value became 141 mg/dl and neutral fat also became 235 mg/dl on 30th day.

She continued to take the composition II of the present invention by 20 g very day. Her blood sugar value was changed from 141 mg/dl to 128 mg/dl and neutral fat was also changed from 235 mg/dl to 143 mg/dl (normal value is 20 mg/dl).

CLINICAL EXAMPLE 6

Adult male (age: 45) with acute pancreatitis, urinous amylase value of 2362 (normal value is 1100 or less) at the time of admission to a hospital:

Upon continuous feeding of the composition II of the present invention by 20 g per day, his urinous amylase value was decreased to 1174 on 7th day.

CLINICAL EXAMPLE 7

Adult male (age: 40) with chronic pancreatitis, diabetes, blood sugar value under his hungry state of 172 mg/dl, diabetes index of (HbAl value) of 8.8:

Upon continuous feeding of the composition I of the present invention by 20 g per day, his blood sugar value after 4 weeks became 145 mg/dl and his diabetes index became 8.1 (a normal value is 7.7 or less).

Upon continuous feeding of the composition II of the present invention by 20 g per day, his blood sugar value under a state of hungry was changed from 145 mg/dl to 119 mg/dl after 20 days. His diabetes index became 7.5 (a normal value is 7.7 or less).

CLINICAL EXAMPLE 8

Adult male (age: 66) with hyperlipidemia:

Upon continuous feeding of the composition I of the present invention by 10 g per day, his neutral fat value was changed from 499 mg/dl to 315 mg/dl after 30 days.

Upon continuous feeding of the composition II of the present invention by 10 g per day, his neutral fat value was changed from 315 mg/dl to 184 mg/dl after 30 days.

CLINICAL EXAMPLE 9

Adult female (age: 72) with hyperlipidemia and neutral fat value of 280 mg/dl:

Upon continuous feeding of the composition II of the present invention by 20 g per day, her neutral fat value became 156 mg/dl after two weeks. High blood pressure value of about 168 mmHg to 183 mmHg was stabilized at a value ranging from an upper blood pressure value of 152 mmHg to a lower blood pressure value of 96 mmHg in ±5.

CLINICAL EXAMPLE 10

Adult male (age: 66) with diabetes, hepatosis, postprandial blood sugar value of 337 mg/dl, neutral fat value of 287 mg/dl:

Upon continuous feeding of the composition I of the present invention by 20 g per day, his blood sugar value became 288 mg/dl and neutral fat value became 237 mg/dl in two weeks.

Upon continuous feeding of the composition II of the present invention by 20 g per day, his blood sugar value was decreased from 288 mg/dl to 231 mg/dl. His neutral fat value was changed from 237 mg/dl to 175 mg/dl.

CLINICAL EXAMPLE 11

Adult male (age: 69) with diabetes; insulin injection therapy; blood sugar value of 326 mg/dl.

Upon continuous feeding of the composition I of the present invention by 20 g per day, his blood sugar value became 209 mg/dl in 60 days.

Upon continuous feeding of the composition II of the present invention by 20 g per day, his blood sugar value was changed from 209 mg/dl to 154 mg/dl in 20 days.

ANOTHER CLINICAL EXAMPLE

Maltese, female (age: 14), weight of 3.5 kg; Visual acuity is weakened; and gait disorder:

Continued feeding of the composition II by 1.2 g per day caused its disease to be recovered in 14 days and enabled it to make a tottering step. Further in 14 days, its weight was decreased down to 3.1 kg and its walking was made easy.

As described above, it can be confirmed that the undevitalized fortified composition of the present invention has superior pharmacodynamics as found in a herb medicine of providing suppression against onset of type I autoimmunization diabetes, type II diabetes and amelioration of hyperlipidemia.

This can be considered that sugar chains, some enzymes not losing capability of catalysis and nutritive substances such as vitamins and minerals contained in this composition are efficiently digested and absorbed, apply energy as synergism, contribute to environmental improvement of the internal tissue cells, relate to recuperation of sugar chain of lost cells, provide recuperation of inter-cell cognizance function, activate metabolism and further activate regeneration of cell as well as immune function.

Although a feeding amount of the composition of the present invention is increased or decreased in response to composition of a patient, pathosis and a degree of disease or the like, it is preferable to apply about 20 g per day for an adult person as average value and about 10 g per day is sufficient for keeping a healthy condition.

2. Effects of Invention

The present invention constituted as described above has some superior effects as follows.

(1) The invention described in Claim 1 is made such that *aspergills oryzae* strain colony is cultivated under a state in which embryo bud and *garnoderma lucidum* are mixed to each other, ripened and both starch and protein or the like are completely decomposed into low molecules and they are easily absorbed. Although the species contained in the ripened product are diminished, the groups of enzyme are kept at a state in which capability of catalysis of enzyme itself is not lost and kept slept. Since vitamins are fortified to this product, taking of the product causes enzyme to attain coenzyme action of vitamins, activates various kinds of action provided by enzyme, supplements nutritious substances against attenuation in metabolism under synergism of various kinds of contained substances included in the suppression composition, gives energy and improves environment of the internal tissue, so that the present invention has some effects that it may promote a healthy state of human, activate metabolism function and immunity function held by the human tissue cells proper, suppress against onset of diabetes as well as complication of it.

(2) In the present invention described in Claim 2, some vitamins are selectively mixed from the groups of vitamin B, so that when vitamins $B_1$, $B_{12}$ are selected, they may have some effects that they contribute to metabolism of amino acid and biosynthesis of protein and the like to promote metabolism, improve environment of cell in synergism manner, activate human body tissue cells as well as immunity function, suppress onset of diabetes and effective suppression of complication.

(3) In the present invention described in Claim 3, the groups of vitamins $B_1$, $B_6$, $B_{12}$ are sufficiently mixed, coenzyme action may improve an absorbing power of nutritious substances under synergistic effect for activating sufficiently enzyme of composition, supply high energy, promote metabolism, activate human body tissue cells as well as immunity function and contribute to suppression of onset of diabetes and improvement of hyperlipidemia of complication as well as high blood sugar value.

(4) In the present invention described in Claim 4, internal oxidation or reducing action provided by vitamin C and coenzyme action against hydrogen transmission enzyme system may act in a synergistic manner, remarkably improve environment of internal tissue cells, provide a superior diminishing activity against internal active oxygen under application of specified amount of composition, recover an acknowledging function of inter-cells, improve metabolism as well as flood flow, improve immunodeficiency, improve allergy, suppress onset of diabetes, in particular, onset of type I diabetes, promote proliferation and differentiation of pancreas β-cells and improve complication and the like.

(5) In the present invention described in Claim 5, suppression of internal lipid peroxide and improvement of deficiency in peripheral blood vessels held by vitamin E may act in a synergism manner and remarkably improve environment of internal tissue cells and when a specified amount of the composition is taken, it has a superior diminishing activation against internal lipid peroxide, improve metabolism of lipid, blood flow, immunodeficiency and allergy and has some effects on suppression against onset of diabetes, in particular, suppression against onset of type I diabetes, promoting proliferation and differentiation of pancreas β-cells and improving complication and the like.

(6) In the present invention described in Claim 6, special raw materials suitable for a domestic dog are added to the composition and the composition is easily edible by the domestic dog, so that the composition may easily be fed to the domestic dog. A specified amount of composition has some effects to recover a health condition of a dog getting old, attenuating metabolism function, getting too fat or weakened leg muscle.

Although the present invention has been described with reference to the preferred embodiments, it is apparent that the present invention is not limited to the aforesaid preferred embodiments, but various modifications can be attained without departing from its scope.

What is claimed is:

1. A composition used to treat diabetes made by the following process:
    a) mixing an isolated embryo bud and isolated seed coat from rice with a fruit body of *Ganoderma lucidum* to form a mixture;
    b) fermenting said mixture with an *Aspergillus oryzae* strain to produce a resulting fermentate;
    c) drying the resulting fermentate to produce a dried fermentate;
    d) crushing the dried fermentate into a fine powder; and
    e) mixing the powder with vitamin B to form said composition.

2. The composition of claim 1, wherein said vitamin B is selected from the group consisting of vitamin $B_1$, vitamin $B_6$ and vitamin $B_{12}$.

3. The composition of claim 1, wherein said composition further comprises vitamin C.

4. The composition of claim 1, wherein said composition further comprises vitamin E.

5. The composition of claim 1, wherein said powder has a moisture content of 4% or less.

* * * * *